United States Patent [19]

Bradley et al.

[11] Patent Number: 4,576,170

[45] Date of Patent: Mar. 18, 1986

[54] HEART MONITOR AND DEFIBRILLATOR DEVICE

[75] Inventors: Robert F. Bradley; Lindell P. Bradley, both of New Buffalo, Mich.

[73] Assignee: Micro-Circuits Company, New Buffalo, Mich.

[21] Appl. No.: 167,382

[22] Filed: Jul. 9, 1980

[51] Int. Cl.⁴ ............................................. A61N 1/32
[52] U.S. Cl. ............................... 128/419 D; 128/639; 128/798
[58] Field of Search ................... 128/419 D, 639, 640, 128/798, 802, 702, 704, 705, 706

[56] References Cited

U.S. PATENT DOCUMENTS

| | | | |
|---|---|---|---|
| 2,943,628 | 7/1960 | Howell | 128/640 |
| 3,093,136 | 6/1963 | Lohr | 128/419 D |
| 3,138,151 | 6/1964 | Chapman et al. | 128/705 |
| 3,426,746 | 2/1969 | Seamans, Jr. | 128/640 |
| 3,464,404 | 9/1969 | Mason | 128/640 |
| 3,857,398 | 12/1974 | Rubin | 128/419 D |
| 4,023,573 | 5/1977 | Pantridge et al. | 128/419 D |
| 4,096,856 | 6/1978 | Smith et al. | 128/419 D |
| 4,129,125 | 12/1978 | Lester et al. | 128/702 |
| 4,243,051 | 1/1981 | Wittemann | 128/802 |

FOREIGN PATENT DOCUMENTS 272021  7/1964  Australia ..................... 128/419 D Primary Examiner—William E. Kamm
Attorney, Agent, or Firm—Marmaduke A. Hobbs

[57] ABSTRACT

A heart monitor and defibrillator device, which can be worn by high risk patients with only minimal interference with normal daily activities, in which one pocket-size unit contains a heart monitor and microprocessor and a second pocket-size unit contains defibrillation circuitry. ECG electrodes are attached to the patient to sense heart impulses and transmit the impulses to the first unit, which analyzes the heart beat and determines if defibrillation is required. The second unit administers the defibrillating shock when required and has a built-in delay so that the wearer is warned to prepare for defibrillation. Several defibrillation shocks may be administered at spaced intervals. The defibrillation electrodes include layers of electrically conductive, skin adhering paint having low contact resistance, and the electrodes may be moved by the patient to prevent skin irritation in the electrode site.

15 Claims, 7 Drawing Figures

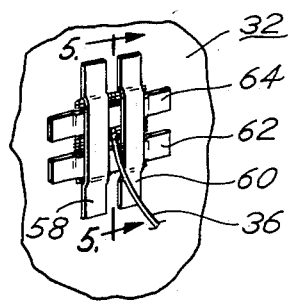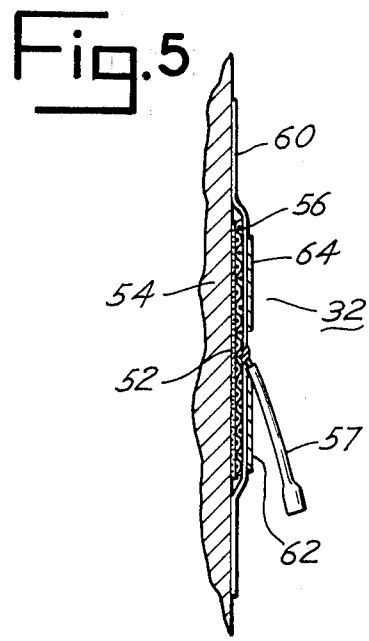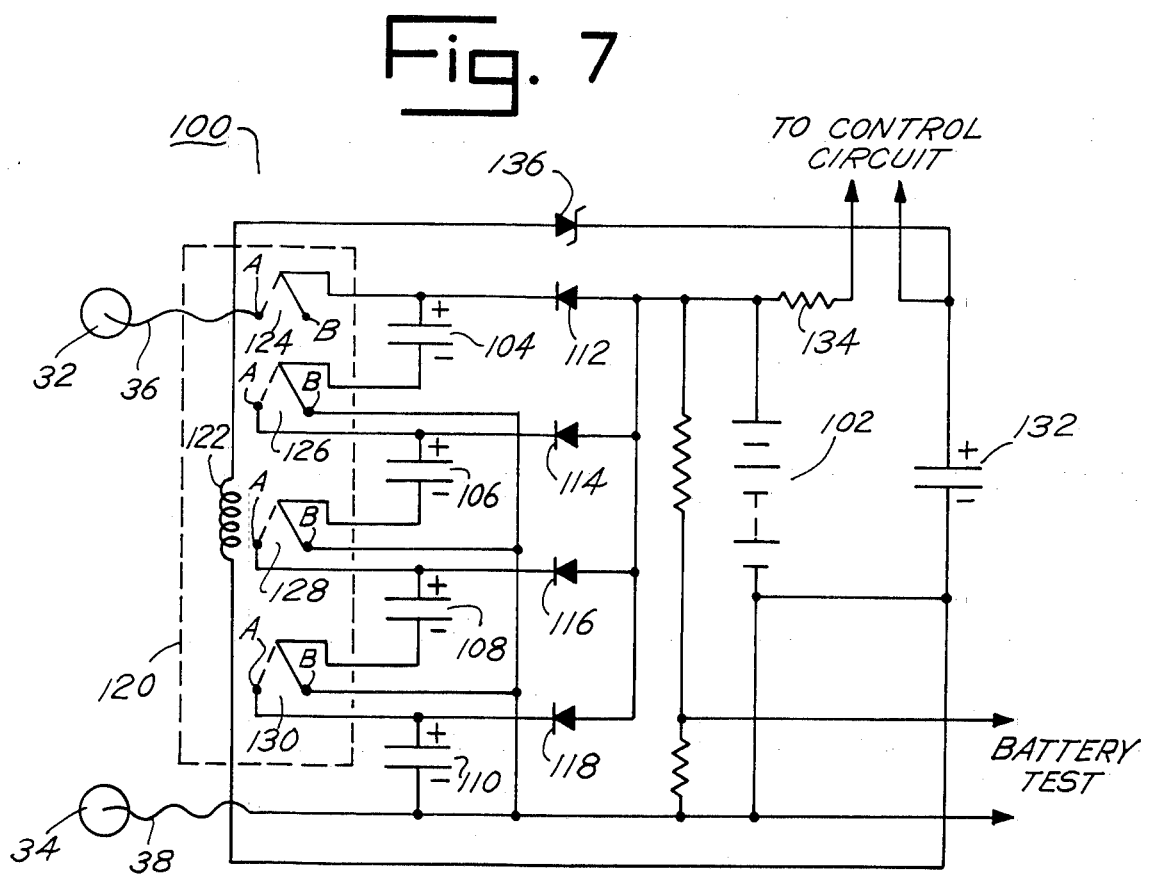

HEART MONITOR AND DEFIBRILLATOR DEVICE

Coronary heart disease is one of the leading causes of death in the United States and other developed countries. Many of the victims of this disease die suddenly, before medical assistance can arrive, even though a substantial number of the victims may have been known to be in a group having a high risk of death resulting from heart disease. Members of the high risk group include those persons having previous heart ailments, including those who have experienced myocardial infarctions, ventricular arrhythmias and other heart irregularities.

One of the forms of coronary heart disease most frequently causing death is ventricular fibrillation, which occurs when the normal and regular electrical impulses initiated by the heart are replaced by irregular and rapid impulses, causing the heart muscle to stop normal contractions and to begin to quiver. Normal blood flow ceases, and organ damage or death may result in minutes if normal heart contractions are not restored. Although frequently not noticeable to the victim, ventricular fibrillation is often preceded by ventricular tachycardia, which is a regular but fast rhythm of the heart. Normal heart function can be restored to a person suffering ventricular fibrillation or ventricular tachycardia by a procedure known as cardioversion, the application of electric shock through the heart muscle. Defibrillators of various types have been used extensively for this purpose; however, conventional defibrillators are commonly found only in hospitals and other health care facilities. Since the victim often has no noticeable warning of the impending fibrillation, death often occurs before the necessary medical assistance can arrive. Even when hospitalized, an ambulatory patient, who is not attached to heart monitoring equipment, may suffer ventricular fibrillation and die before help can arrive. Since death can result within minutes of the onset of fibrillation, patients who would otherwise be able to move about the hospital have been confined to their beds attached to heart monitors, to notify nursing personnel of the onset of fibrillation. This increases the personal mental trauma which a cardiac patient suffers, by increasing the feelings of incapacity and dependence upon others. Patients who might otherwise be released from the hospital may be kept at the hospital, only because of the increased risk of ventricular fibrillation.

Since a substantial number of heart fibrillation victims are known to be in a high risk group, attempts have been made to design portable heart monitors and/or defibrillators which the potential victim can wear during the period of greatest vulnerability to fibrillation, which may be as long as one year after the occurrence of previous heart ailments, or in some cases even longer. Thus, a portable personal device, which can be worn by the potential victim with little or no physical discomfort, is necessary. Since the patient is often otherwise healthy, and suffers only from the increased possibility of ventricular fibrillation, a personal heart monitor and defibrillator device must be small enough to be carried by the patient without interfering with normal daily activities, and should be simple enough for the potential victim to attach on his own. Previous monitor and/or defibrillator devices to be worn by ambulatory patients have used needles or probes inserted through the chest wall and into the heart, or cardiac catheters inserted into the heart through the superior venacava. One of the primary difficulties previously encountered, which made necessary the use of internal heart probes, is that for effective cardioversion of the heart, the contact between the defibrillation electrodes and the patient must have a low contact resistance. To be effective, defibrillating shock charges administered through electrodes having higher contact resistances must be of higher energy levels than shock charges administered through electrodes having lower contact resistances. Skin damage in the area of the electrode placement may result if contact resistance is too high. Previously, it was believed that an adequate external contact for the high amperage defibrillator discharge could be achieved only through the use of large defibrillator paddles pressed with relatively great force against the skin. This was impractical for use on portable devices to be worn continuously; hence, the internal electrode probes were thought to be preferable, and invasive surgical procedures were required for the use of the prior defibrillators.

It is therefore one of the principal objects of the present invention to provide a combination heart monitor and defibrillator device which will sense ventricular fibrillation or other heart irregularities and initiate a defibrillating shock charge in response thereto, and which can be worn comfortably by an ambulatory patient over an extended period of time with only a minimal amount of inconvenience to normal daily activities.

Another object of the present invention is to provide a heart monitor and defibrillator device which has monitoring and defibrillating electrodes that provide adequate patient contact without penetration of the chest wall, and which warns the wearer prior to the discharge of a defibrillating shock charge to allow the wearer to prepare for defibrillation.

A further object of the present invention is to provide a heart monitor and defibrillator device which will monitor the heart condition after the discharge of a defibrillating shock charge, and which will administer subsequent defibrillation shock charges if required, the subsequent shocks being given at spaced intervals.

A still further object of the present invention is to provide a heart monitor and defibrillator device which has monitor and defibrillator electrodes that can be applied by the patient, thus enabling the patient to move the location of the electrodes among a set of previously marked locations to promote better skin health in the area of the electrode attachment, and which has defibrillator electrodes that make contact with the patient's skin with low contact resistance, with little or no pressure or discomfort, and which may be shaped and positioned to most effectively administer defibrillating shock charges.

Additional objects and advantages of the present heart monitor and defibrillator device will become apparent from the following detailed description, and the accompanying drawings, wherein:

FIG. 4 is a perspective view of a preferred embodiment of one of the defibrillator electrodes of the present invention;

FIG. 5 is an enlarged cross-sectional view of the defibrillator electrode shown in FIG. 4, taken on line 5—5 of the latter figure;

FIG. 6 is a cross-sectional view, similar to that shown in FIG. 5, of a modified form of the defibrillator electrode; and FIG. 7 is a schematic view of a preferred embodiment of the defibrillator circuit.

Figure 1:
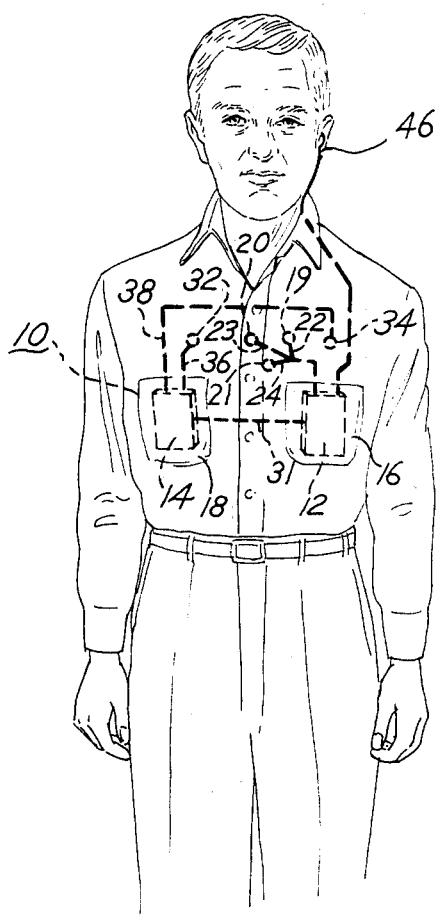
FIG. 1 is a perspective view showing one manner in which a heart monitor and defibrillator device of the present invention may be worn.
Figure 2:
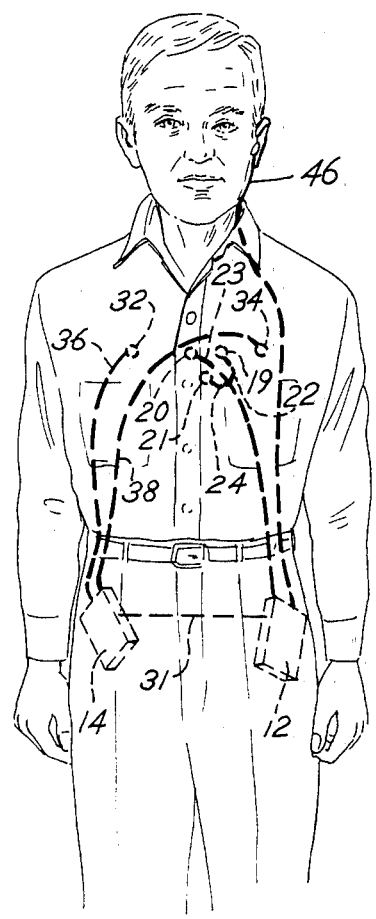
FIG. 2 is a perspective view showing an alternative manner for wearing the present heart monitor and defibrillator device.
Figure 3:
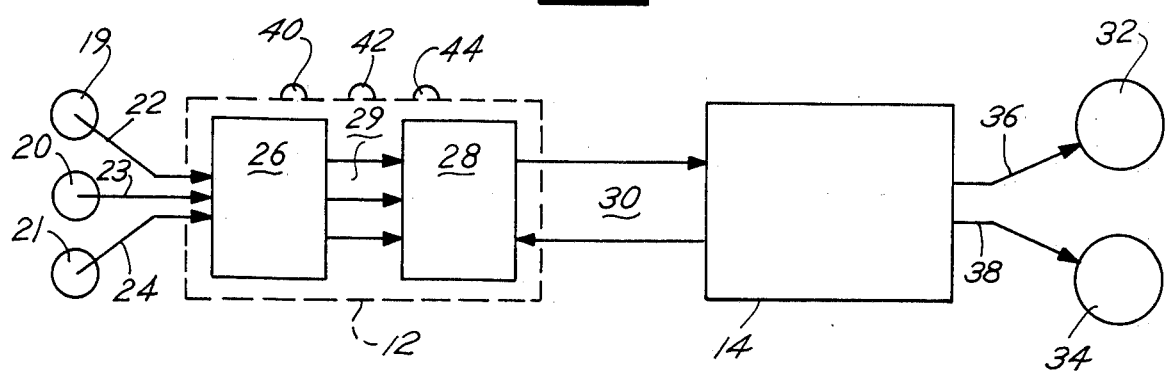
FIG. 3 is a schematic view of the heart monitor and defibrillator device.

Referring more specifically to the drawings and to FIG. 1 in particular, numeral 10 designates a heart monitor and defibrillator device embodying the present invention, having a monitor/microprocessor assembly 12 and a defibrillator assembly 14, each of which is about the size of a pack of cigarettes and can be carried in shirt pockets 16 and 18 as shown. FIG. 2 shows an alternative manner for carrying heart monitor and defibrillator device 10, wherein microprocessor assembly 12 and defibrillator assembly 14 are worn in trouser pockets instead of the shirt pockets as shown in FIG. 1. Except for longer lead wires to the various monitor and defibrillator electrodes, the assemblies of FIG. 2 are the same as those shown in FIG. 1.

ECG electrodes 19, 20 and 21 are provided for sensing the small voltages resulting from the functioning heart and are connected by wire leads 22, 23 and 24 to the microprocessor assembly 12. The electrodes may be of any of the commercially available types which can be applied quickly to the patient's skin and kept in place for several days. Microprocessor assembly 12 includes an ECG amplification unit 26 and a programmed microprocessor 28, connected to each other by a connecting link 29 to transmit electronic signals therebetween. Amplification unit 26 receives the ECG voltages sensed by electrodes 19, 20 and 21 and amplifies and sorts the voltages before relaying them to microprocessor 28. The circuitry of amplification unit 26 includes many complex electronic functions on minute electronic chips; thus, amplification unit 26 receives the ECG voltages, preamplifies the voltages, and sorts the signals by frequency, sequence and amplitude so that the signals relayed to programmed microprocessor 28 are received in a state whereby the microprocessor may make analyses based on the input signals.

The signals received by microprocessor 28 may initiate any one of several functions within the microprocessor. Defibrillator assembly 14 is connected to microprocessor 28 by a harness 30, and is controlled by the microprocessor so that a defibrillating shock is administered when the microprocessor determines that the heart is in a fibrillating condition. The shock charge is administered through defibrillator electrodes 32 and 34 connected to defibrillator assembly 14 by leads 36 and 38. The programmed microprocessor contains warning and sensing circuitry which activates a warning mechanism to inform the wearer that a defibrillation shock will be initiated shortly. This affords the person wearing the monitor and defibrillator device an opportunity to lie down or otherwise prepare for defibrillation. The warning circuitry of microprocessor 28 should also include a warning when the battery or other electrical source of defibrillator 14 is sufficiently low that an ineffective defibrillation shock would result. Warnings of other system malfunctions may also be incorporated into the warning circuitry of microprocessor 28. A series of light emitting diodes 40, 42 and 44 or similar devices on the monitor/microprocessor assembly may be used to indicate system malfunctions or impending defibrillation shock. Each of the lights should indicate a different irregularity to fully inform the wearer of either a system malfunction or impending defibrillation. A pneumatic or electric earplug 46 may be used, and a series of beeps or other sounds initiated by the microprocessor will inform the wearer of the condition sensed by the microprocessor; thus a steady tone may indicate that defibrillation will occur soon, a series of short beeps may indicate that the unit's battery is dangerously low, or other auditory signals may be given. Those skilled in the art, using micro-circuitry techniques, will be able to build amplification units and programmed microprocessors of the size previously stated.

To provide semipermanent defibrillator electrodes of low contact resistance, electrically conductive skin adhering paint is used. A conductive paint layer 52 is applied to the skin 54 of the patient. A suitable electrically conductive skin paint for use in defibrillator electrodes is paint number SC20 from Micro-Circuits Company, which adheres to skin with little discomfort to the wearer, even when worn for extended periods of time, and which has a low contact resistance to minimize skin damage from the defibrillation shock charge. A wire mesh 56 having a disconnectable terminal 57 soldered thereto, is placed on the paint layer and held firmly in contact therewith by surgical tape strips 58, 60, 62 and 64. Terminal 57 is attached to a lead wire from the defibrillator. When a defibrillation shock is initiated, the current is conducted through the lead to the wire mesh 56 and is distributed evenly by the wire mesh to the conductive paint layer 52. Since a very low contact resistance exists between paint layer 52 and the skin 54, little or no skin damage will result from the defibrillation shock charge. The intimate contact between the skin and paint distributes the shock over the entire area of skin beneath the paint layer.

It may be desirable in some applications for a layer of conductive paint to be applied over the wire mesh 56 so that the wire mesh is completely enclosed within a paint layer 70 as shown in FIG. 6. The second paint layer more fully ensures the even distribution of the electric charge from the wire mesh to the painted area, in that the second layer of paint flows around the wire strands of the wire mesh and prevents the possibility of the mesh having areas of wrinkles or bubbles which would not contact the paint layer. The mesh becomes completely enclosed within the paint. Protective tape strips 72, 74 and 76 may be used to cover the combined paint-mesh-paint electrode.

FIG. 7 is a schematic view of a preferred circuit 100 for the discharge of a defibrillating shock charge. A battery 102 is the energy source for the circuit and will normally be of the compact type used extensively in electronic equipment, in the range of 240 volts to 510 volts. A plurality of capacitors 104, 106, 108 and 110 are charged by battery 102 through diodes 112, 114, 116 and 118. Capacitors 104, 106, 108 and 110 are interconnected through a four-pole, double-throw relay indicated by the box in phantom lines designated with numeral 120. Relay 120 has a coil 122 and contacts 124, 126, 128 and 130, each with positions A and B. When no current is introduced to coil 122, the contacts are in position B, shown by the solid lines in the drawing, and capacitors 104, 106, 108 and 110 are in parallel connection for charging from battery 102. Activation of coil 122 moves contacts 124, 126, 128 and 130 to position A, shown by the dotted lines in the drawing, wherein the capacitors are in series connection for discharging a defibrillating shock charge through defibrillating electrodes 32 and 34. By combining different numbers of capacitors with batteries of various voltages, defibrillating discharge voltages within a wide range can be achieved. Preferably, capacitors 104, 106, 108 and 110 will be of a low leakage type so that battery 102 can maintain a full charge in the capacitors for a month or longer, while retaining sufficient reserve potential to recharge the capacitors for additional defibrillating shock charges if required.

To provide a time period during which the patient may prepare for the defibrillating shock by lying down or the like, the activation circuit for coil 122 contains a capacitor 132 which will normally be uncharged. Battery 102 and a resistor 134 are connected to capacitor 132 through the microprocessor assembly 12, which closes the circuit between battery 102 and capacitor 132 only when ventricular fibrillation has been sensed and confirmed by the microprocessor. Capacitor 132 will charge from battery 102 through resistor 134 in perhaps 15 to 30 seconds after ventricular fibrillation has been detected and the patient warning signal has been given. A Zener diode 136 or other appropriate switching circuitry, is connected between capacitor 132 and coil 122 of relay 120, and is activated by the charging voltage of capacitor 132, permitting the discharge of the capacitor through coil 122 when the capacitor charge approaches the voltage of battery 102. The discharge of capacitor 132 through coil 122 will cause contacts 124, 126, 128 and 130 to move to position A, placing capacitors 104, 106, 108 and 110 in series connection to produce a defibrillating shock charge across electrodes 32 and 34.

When capacitor 132 has discharged sufficiently, the current through coil 122 will drop and contacts 124, 126, 128 and 130 will return to position B wherein capacitors 104, 106, 108 and 110 are in parallel connection for recharging from battery 102. If the monitor/microprocessor assembly 12 has sensed that fibrillation has stopped, the circuit between battery 102 and capacitor 132 will open. Capacitors 104, 106, 108 and 110 will recharge, and the defibrillator will then be in readiness for a future defibrillating discharge if assembly 12 senses fibrillation and closes the circuit to capacitor 132, enabling the capacitor to charge and activate coil 122.

If, following discharge of the defibrillating shock charge, the microprocessor senses that fibrillation has not stopped, the circuit between battery 102 and capacitor 132 will remain closed. During the initial stages in which capacitors 104, 106, 108 and 110 are being recharged, the terminal voltage of battery 102 will be at a low level because of the heavy recharging load. As the capacitors approach full charge, the terminal voltage of battery 102 will increase. Since the circuit between the battery and capacitor 132 has remained closed, the charge on capacitor 132 will increase as the terminal voltage of the battery increases. As a result of the delay caused by resistor 134, capacitor 132 will reach the voltage necessary to discharge through Zener diode 136 a short time after capacitors 104, 106, 108 and 110 have reached full charge. A second defibrillating shock charge will be discharged when relay 120 places capacitors 104, 106, 108 and 110 in series connection. Recharge and subsequent discharge of a defibrillation shock charge will continue until the monitor/microprocessor assembly 12 senses that fibrillation has stopped and opens the circuit between battery 102 and capacitor 132, or until battery 102 is exhausted and can no longer charge capacitor 132 sufficiently to discharge through Zener diode 136.

In the use and operation of a heart monitor and defibrillator device embodying the present invention, a patient having a high risk of ventricular fibrillation will be detected as such by his physician. If the patient is not on permanent heart monitoring equipment in an intensive care unit or the like, the physician may choose to use the present heart monitor and defibrillator device. If the patient is to make frequent visits to the doctor, or is an ambulatory patient in a health care facility, the doctor will connect the electrodes to the patient and may periodically change their location slightly, to prevent skin irritation in the area beneath the electrodes. If the patient is an out patient and will make only periodic visits to the doctor, the doctor will select several sets of electrode locations and will use appropriate skin dyes to mark the areas on the patient. Thus, two sets of three ECG electrode locations will be chosen and marked in different colors, and two or more sets of defibrillator electrode locations will also be chosen and marked. In applying the defibrillator electrodes shown in FIGS. 4 through 6, the patient, when changing the electrode location, paints a layer 52 of conductive paint on the chosen site, making sure that an uninterrupted layer is formed over the site. The wire mesh 56 is placed on top of the paint layer 52 and may be secured in place by attaching strips of tape to hold the mesh against the paint layer, or by applying a second paint layer on top of the wire mesh to encapsulate the mesh in the paint. Protective tape may be placed on top of the paint layer if desired, and terminal 57 is connected to the appropriate leads to the defibrillator assembly. After perhaps a week of use at one location, the patient may move the electrodes to the alternative set of attachment sites outlined by his physician. The conductive paint electrodes, which are assembled on the patient, can be shaped and positioned for optimal placement of a defibrillation shock charge. The paint can be applied at the exact location and in the exact shape outlined by the physician, and will distribute the charge in that area.

Normally, amplification unit 26 and microprocessor 28 will be in one small housing, previously referred to as the monitor/microprocessor assembly, and the defibrillation circuitry will be in another assembly, the defibrillator assembly 14. When separated in this manner, each will normally fit in clothing pockets such as the shirt pockets shown in FIG. 1 or the trouser pockets shown in FIG. 2. The units may be combined in a single larger housing which would be worn on the patient's belt, or carried by its own belt or string around the patient's waist, or over the shoulder. The ECG electrodes will continuously receive electrical impulses from the heart muscle and will relay the electrical impulses to amplification unit 26 in which the impulses are amplified, sorted and converted to appropriate impulses to be analyzed and acted upon by the programmed microprocessor 28. The programming of microprocessor 28 may be varied so that only ventricular fibrillation will be detected and acted upon or, in more complex units requiring perhaps a slightly larger microprocessor, atrial fibrillation and other non-fatal conditions may be programmed therein. The warning circuitry of microprocessor assembly 12 will issue warnings when the battery power for the unit is low, when defibrillation shock is to be administered, and perhaps even when electrode contact with the skin is insufficient. Notification of the system irregularities may be accomplished by the light emitting diodes 40, 42 and 44 or, in the preferable embodiment, by an earplug 46 through which warning sounds are transmitted to the patient.

When a heart irregularity has been detected by microprocessor assembly 12, the defibrillator assembly 14 is triggered to administer a defibrillating shock. The heart condition will again be monitored after the defibrillation shock and, if fibrillation continues, subsequent shocks will be administered. In the preferred circuitry shown in FIG. 7, when fibrillation is detected, the circuit between battery 102 and capacitor 132 is closed, thereby allowing capacitor 132 to charge. When the charge on capacitor 132 approaches the voltage level of battery 102, Zener diode 136 will permit capacitor 132 to discharge across coil 122. Contacts 124, 126, 128 and 130 are moved to position A, shown by dotted lines in FIG. 7, thus connecting capacitors 104, 106, 108 and 110 in series. The capacitors, having been previously charged by battery 102, administer a defibrillating shock charge through electrodes 32 and 34. When capacitor 132 is discharged, and current no longer flows through coil 122, contacts 124, 126, 128 and 130 will return to position B wherein capacitors 104, 106, 108 and 110 are in parallel connection for charging from battery 102. If microprocessor assembly 12 senses that fibrillation has ceased, the circuit between battery 102 and capacitor 132 will open. Capacitors 104, 106, 108 and 110 will be charged and the defibrillator will be in readiness to administer future defibrillating charges. If, after a defibrillating shock charge has been administered, microprocessor assembly 12 detects that fibrillation continues, the circuit between battery 102 and capacitor 132 will remain closed. As capacitors 104, 106, 108 and 110 approach full charge, the terminal voltage of battery 102 will rise. A short time after the defibrillating capacitors reach full charge, capacitor 132 will reach full charge, the time delay being determined by resistor 134. When capacitor 132 again reaches the prescribed charge level, Zener diode 136 will permit the discharge thereof through coil 122, thereby again moving contacts 124, 126, 128 and 130 so that the defibrillating capacitors are in series connection and a defibrillation charge is administered.

Normally, a patient wearing a heart monitor and defibrillator device embodying the present invention will carry replacement sets of batteries, as battery packs of convenient size will normally last for only a month or so keeping defibrillating capacitors at full charge. When the battery becomes low, warning signals will be transmitted to the patient, either by the light emitting diodes 40, 42 and 44 or by sounds through earplug 46, so that he may change the battery.

By making small holes in his shirt pockets or trouser pockets, a patient using the present heart monitor and defibrillator device can wear the device with little or no detection by others that it is being worn. The two assemblies are easily carried in clothing pockets and the electrode leads can be worn comfortably underneath clothing. The low contact resistance defibrillator electrodes described herein permit the frequent relocation thereof, so that excessive skin irritation does not occur. The present unit is small enough and light enough that it may be worn for weeks, months, or even years, if required, with little or no patient discomfort, and with only a minimal amount of personal inconvenience to the patient. Patients having a high risk of ventricular fibrillation may always have a personal defibrillating unit with them, which can administer perhaps three or four defibrillating shock charges within minutes of the onset of defibrillation. Use of the present monitor and defibrillator can save many lives each year, lives which can be saved only if medical assistance is immediately available. With the present monitor and defibrillator each high risk patient can carry that medical assistance with him at all times.

Although one heart monitor and defibrillator device has been described in detail herein, various changes may be made without departing from the scope of the present invention.

We claim:

1. A heart monitor and defibrillator device for continuously monitoring heart functions and automatically administering defibrillating shock charges, comprising sensing electrodes for continuously detecting heart impulses, amplification means for intensifying and sorting the heart impulses detected by said sensing electrodes, microprocessor means receiving the impulses from said amplification means for analyzing the impulses and determining when a defibrillation shock charge is required, defibrillation circuitry controlled by said microprocessor means having automatic recharge capabilities, a delay means for discharging a defbrillation charge a short time after the necessity of defibrillation is detected by said microprocessor means, warning means for notifying the patient before a defibrillation shock charge is administered, and defibrillator electrodes to be attached to the patient's chest for administering the defibrillation shock charge to the patient's heart.

2. A heart monitor and defibrillator device as defined in claim 1 in which a first housing surrounds said amplification means and said microprocessor means, and a second housing surrounds said defibrillation circuitry.

3. A heart monitor and defibrillator device as defined in claim 1 in which said warning means includes a light emitting diode.

4. A heart monitor and defibrillator device as defined in claim 1 in which said warning means includes an earplug for conveying a signal to the patient.

5. A heart monitor and defibrillator device as defined in claim 1 in which said defibrillator electrodes include a layer of skin adhering electrically conductive paint, wire mesh in low resistance contact with said paint layer, securing means for holding said wire mesh in electrical contact with said paint layer, and connecting means for conducting a defibrillation shock charge from said defibrillation circuitry to said wire mesh.

6. A heart monitor and defibrillator device as defined in claim 5 in which said securing means is a second layer of electrically conductive paint disposed on said wire mesh and bonded to said first paint layer to encapsulate said mesh.

7. A heart monitor and defibrillator device as defined in claim 5 in which said securing means is a plurality of adhesive strips.

8. A heart monitor and defibrillator device as defined in claim 7 in which said defibrillation circuitry includes a battery means for supplying electrical energy, a plurality of capacitors for holding a dischargeable shock charge of cardioverting potential, a four-pole double-throw relay having contacts electrically connected to said capacitors to place said capacitors in parallel connection for charging from said battery means and to change the connection of said capacitors to series connection for discharge of a shock charge of cardioverting potential, a triggering capacitor for said relay, circuit means connecting said battery means and said triggering capacitor through said microprocessor means for charging said capacitor when said circuit means is closed by said microprocessor means, a resistor in said circuit means between said battery means and said triggering capacitor, and an electrical connection from said triggering capacitor to said relay having a Zener diode therein.

9. A heart monitor and defibrillator device as defined in claim 1 in which said defibrillation circuitry includes a battery means connected thereto for supplying electrical energy, storage means for holding a dischargeable shock charge of cardioverting potential, and triggering means for releasing said shock of cardioverting potential.

10. A heart monitor and defibrillator device as defined in claim 9 in which said storage means includes a plurality of capacitors connected in parallel arrangement for charging by said battery means, and a relay for switching said capacitors to a series connection by said triggering means for release of a shock charge of cardioverting potential.

11. A heart monitor and defibrillator device as defined in claim 10 in which said triggering means includes a capacitor charged by said battery means when said microprocessor means closes a connection therebetween, a four-pole double-throw relay having a contact for each of said capacitors of said plurality of capacitors, one position of said contacts being for parallel connection of said capacitors of said plurality of capacitors, the other position of said contacts being for series connection of said capacitors of said plurality of capacitors, and a Zener diode disposed in an electrical connection between said relay and said triggering means capacitor.

12. A heart monitor and defibrillator device as defined in claim 11 in which said delay means includes a resistor in electrical connection between said battery means and said triggering means capacitor.

13. In a heart defibrillator: a defibrillation circuit comprising at least one electrode for delivering an electric charge to a patient, a sensor for detecting heart impulses and creating a signal therefrom, a battery means for supplying electrical energy, a storage means for holding a charge of cardioverting potential including a plurality of capacitors charged by said battery means, a four-pole double-throw relay having contacts connected to said capacitors to place said capacitors in parallel connection for charging from said battery means and to change the connection of said capacitors to series connection for the discharge of a defibrillation charge, a triggering means for said relay, and means responsive to abnormalities in said heart impulse signals for activating said triggering means to actuate said relay to change the connection of said capacitors into a series connection when the electric charge is to be transmitted to said electrode.

14. In a defibrillator: a defibrillation circuit as defined in claim 13 in which said triggering means includes a capacitor, circuit means for connecting said battery means to said triggering capacitor only when defibrillation is required, a connection from said capacitor of said triggering means to said relay, and a Zener diode disposed in said connection between said relay and said capacitor of said triggering means.

15. In a defibrillator: a defibrillation circuit as defined in claim 14 in which a resistor is disposed in said circuit means between said battery means and said capacitor of said triggering means.

* * * * *